US006291238B1

(12) United States Patent
Wagner et al.

(10) Patent No.: US 6,291,238 B1
(45) Date of Patent: Sep. 18, 2001

(54) METHOD OF IMPROVING THE PRIMARY ENERGY METABOLISM OF MAMMALIAN CELL LINES

(75) Inventors: Roland Wagner; Noushin Irani; Manfred Wirth; Joop Van Der Heuvel, all of Braunschweig (DE)

(73) Assignee: Gesellschaft Fuer Biotechnologische Forschung mbH (GBF), Braunschweig (DE)

( * ) Notice: Subject to any disclaimer, the term of this patent is extended or adjusted under 35 U.S.C. 154(b) by 0 days.

(21) Appl. No.: 09/320,359

(22) Filed: May 26, 1999

(30) Foreign Application Priority Data

Feb. 5, 1999 (DE) ................................................ 199 04 794

(51) Int. Cl.$^7$ .............................. C12N 5/00; C12N 9/00; C12N 1/20; C12N 15/00
(52) U.S. Cl. ...................... 435/325; 435/183; 435/320.1; 435/252.3; 536/23.2
(58) Field of Search ................................. 435/183, 252.3, 435/320.1, 325, 366; 536/23.2

(56) References Cited

PUBLICATIONS

"The Biosynthesis of Threonine by Mammalian Cells: Expression of a Complete Bacterial Biosynthetic Pathway in an Animal Cell", Rees et al., Biochem. J. 309, pp. 999–1007, 1995.
"Recombinant Cyclin E. Expression Activates Proliferation and Obviates Surface Attachment of Chinese Hamster Ovary (CHO) Cells in Protein–Free Medium", Renner et al., Biotechnology and Bioengineering, vol. 47, pp. 476–482, 1995.
"Expression of Human α2,6–Sialyltransferase in BHK–21A Cells Increases the Sialylation of Coexpressed Human Erythropoietin: NeuAc–transfer Onto GalNAc(β1–4)GlcNAc–R Motives", Schlenke et al., Animal Cell Technology, pp. 475–479, 1997.
"Ammonium Ion and Glucosamine Dependent Increases of Oligosaccharide Complexity in Recombinant Glycoproteins Secreted From Cultivated BHK–21 Cells", Gawlitzek et al., pp. 518–528, 1998.
"Intracellular UDP–N–Acetylhexosamine Pool Affects N–Glycan Complexity: A Mechanism of Ammonium Action on Protein Glycosylation", Grammatikos et al., American Chemical Society and American Institute of Chemical Engineers, pp. 410–419, 1998.
"Incorporation of Ammonium Into Intracellular UDP–Activated N–Acetylhexosamines and Into Carbohydrate Structures in Glycoproteins", Valley et al., pp. 401–417, 1999.
"Biochemical Transformation of Mouse Cells by Fragments of Herpes Simplex Virus DNA", Maitland et al., Cell, vol. 11, pp. 233–241, May 1977.

"Gene Transfer and Expression, A Laboratory Manual", Michael Kriegler, Stockton Press, 1990.
"The ATP Requirement for Initiation of Eukaryotic Translation Varies According to the mRNA species", Richard J. Jackson, Eur. J. Biochem. 200, pp. 285–294, 1991.
"DNA Sequences in Chromosomes II and VII Code for Pyruvate Carboxylase Isoenzymes in Saccharomyces Cerevisiae: Analysis of Pyruvate Carboxylase–Deficient Strains", Stucka et al., Mol Gen Genet 229, pp. 307–315, 1991.
"Glucose and Glutamine Metabolism of a Murine B–Lymphocyte Hybridoma Grown in Batch Culture", Fitzpatrick et al., Applied Biochemistry and Biotechnology, vol. 43, pp. 93–116, 1993.
"Profile of Energy Metabolism in a Murine Hybridoma: Glucose and Glutamine Utilization", Petch et al., Journal of Cellular Physiology 161, pp. 71–76, 1994.
"Biochemistry of Growth Inhibition by Ammonium Ions in Mammalian Cells", Ryll et al., Biotechnology and Bioengineering, vol. 44, pp. 184–193 (1994).
"Effect of Vitreoscilla Hemoglobin Expression on Growth and Specific Tissue Plasminogen Activator Productivity in Recombinant Chinese Hamster Ovary Cells", Pendse et al., Biotechnology and Bioengineering, vol. 44, pp. 1367–1370, 1994.
"Citric Acid Cycle," John M. Lowenstein, Methods in Enzymology, vol. 13, pp. 250–258, 1969.
"Genetic Engineering of Hybridoma Glutamine Metabolism," Bell et al., Enzyme and Microbial Technology, vol. 17, pp. 98–106, 1995.
Brightwell et al. Serum dependent and cell cycle dependent expression from a cytomegalovirus–based mammalian expression vector. Gene, 1997, vol. 194:115–123, 1997.*
Hobbs et al. Development of a bicistronic vector driven by the human polypeptide chain elongation factor 1 alpha promoter for creation of stable mammalian cell lines that express very high levels of recombinant proteins. Biochem. Biophys.Res. Comm. vol. 25, 1998.*
Morris et al. Yeast carboxylase:gene isolation. Biochem. Biophys. Res. Comm. vol: 145: 390–396. 1987.*
Neerman et al. Comparative analysis of glucose and glutamine metabolism in transformed mammalian cell lines, insect and primary liver cells. J. Cellular Physiol. vol. 166:152–169. 1996.*

* cited by examiner

Primary Examiner—Rebecca E. Prouty
Assistant Examiner—Manjunath Rao
(74) Attorney, Agent, or Firm—Marshall, O'Toole, Gerstein, Murray & Borun

(57) ABSTRACT

The invention relates to a method of improving the primary energy metabolism of mammalian cell lines, in which by means of genetic engineering a structural gene for a cytoplasmic yeast pyruvate carboxylase is inserted into the mammalian cells and expressed.

15 Claims, 5 Drawing Sheets

METHOD OF IMPROVING THE PRIMARY ENERGY METABOLISM OF MAMMALIAN CELL LINES

The invention relates to a method of improving the primary energy metabolism of mammalian cell lines, to expression vectors for use in the method and to recombinant mammalian cells having improved primary energy metabolism obtainable in accordance with the method.

Only a very small proportion of glucose, which is one of the main sources of energy, can be fully oxidised to $CO_2$. The majority is released as lactate and alanine. Since the amount of energy gained in aerobic glycolysis is only very small, the energy requirement is met by glutaminolysis, in which ammonium is formed as a toxic by-product.

Various studies have shown that the crucial enzymes that transfer the end product of glycolysis, pyruvate, into the citric acid cycle (TCA) have only weak activity in cell lines (Fitzpatrick et al., 1993; Petch and Butler, 1994; Neermann and Wagner, 1996) (a list of the quoted literature references will be found at the end of this description). If there is a connection between glycolysis and the citric acid cycle, it will increase the contribution of glucose to energy metabolism and reduce the glutamine requirement.

Overview of Energy Metabolism in Mammalian Cell Lines

For culturing of permanent mammalian cell lines, glucose and glutamine occupy a special position amongst the numerous essential components of the relatively complex nutrient medium because, unlike in the case of bacteria or yeasts, both substrates are necessary as suppliers of energy, glutamine serving as a primary source of cellular energy (ATP). The degree of cellular energy supplied by glutamine depends on the individual cell line and on the presence and concentration of glucose.

The primary energy metabolism of mammalian cells is therefore composed of glucose and glutamine oxidation and includes the metabolic pathways of glycolysis, glutaminolysis and the citric acid cycle. A simplified overview of those primary metabolic pathways with branches and crucial enzyme functions is given in FIG. 1.

Glucose Metabolism

In mammalian cell lines, between 80% and 97% of the glucose is converted by means of glycolysis. In contrast to insect or primary cells, however, in transformed mammalian cell lines almost all the glucose converted in glycolysis is processed to lactate, and only a very small proportion (about 0.2 to 5%) of the glucose carbon, i.e. the glycolytic intermediates, passes into the energysupplying citric acid cycle.

It is largely unexplained why glucose is converted almost completely into lactate and the transition of glycolytic intermediates into the citric acid cycle is blocked in the case of almost all mammalian cell lines.

An initial supposition is that the activity of the mediating enzyme pyruvate dehydrogenase is very low as a result of low expression rates or permanent inhibition by irreversible phosphorylation. As a result of that false regulation, large amounts of lactate are secreted into the nutrient medium where they lead to uncontrolled acidification of the culture. Those factors result in a low degree of efficiency in the utilisation of the nutrients, high glucose consumption and a low energy yield.

Glutamine Metabolism

Unlike glycolysis, glutaminolysis is not a single, complete metabolic pathway, but forms a network of up to eight, partly interconnected, alternative metabolic pathways by which glutamine can be oxidised to different degrees and which therefore result in different energy yields and product combinations.

A large proportion of the glutamine is deaminated and introduced via the intermediate a-ketoglutarate into the citric acid cycle where it can be fully oxidised to $CO_2$. In addition, glutamine may also be converted partly into the amino acids aspartate and alanine, and also into lactate. These may either be secreted into the culture medium or, in the case of aspartate, introduced into the citric acid cycle via oxaloacetate.

The choice of the pathways to the complete or only partial oxidation of the glutamine decides the contribution of glutamine to the energy balance of the cell. Investigations carried out on various mammalian cell lines have shown that glutamine in the presence of glucose meets from 30% to 65%, and possibly even up to 98%, of the cell's energy requirement. In general, the contribution of glutamine to the energy balance of the mammalian cell is higher, the lower the concentration of glucose in the medium.

A crucial by-product of glutamine breakdown is ammonium. Depending upon the glutaminolytic metabolic branch, one or two moles of ammonium may be released per mole of glutamine, this having a growth-inhibiting to toxic effect on the cells. On the one hand, the intracellular pH value is lowered, while on the other hand large amounts of ammonium result in changes to the nucleotide and sugar-nucleotide pool (Ryll et al., 1994; Valley et al., 1999), which has a significant effect on the expression of the N-glycosidically bonded carbohydrate side chains of glycoproteins and thus alters the product quality of therapeutic agents (Gawlitzek et al., 1998; Grammatikos et al., 1998).

Metabolic Engineering in Mammalian Cell Lines

Attempts to achieve a significant improvement in the growth and productivity of cellular systems probably require the radical modification of certain substrate streams of the energy metabolism. For that purpose, very accurate information relating to key points of the metabolism are necessary.

Since, however, it is precisely in sensitive mammalian cells that an irreversible intervention in metabolism is associated with considerable difficulties, only very few attempts to obtain a rational design of the metabolism have been carried out successfully in mammalian cells, as compared with bacteria and yeasts.

In fact, according to present knowledge only six successful attempts at metabolic engineering in the so-called primary metabolism of mammalian cells have taken place.

The first approach in mammalian cell lines was disclosed by Pendse and Bailey (1994). On the assumption that an increase in the innercellular ATP or energy level would raise productivity, the gene for the bacterial Vitreoscilla haemoglobin (Vhb) was cloned into a tPA-producing CHO cell line. In comparison with a non-transfected control cell line, the resulting Vhb-expressing cell line exhibited a reduction in growth, but a 40% to 100% increase in specific tPA production. It is clearly possible to influence both growth and productivity by way of increased cellular energy states.

Renner et al. (1995) established a connection between cell cycle phases, growth and cyclin-E expression through experiments with growth factors such as bFGF (basic fibroblast growth factor). Where cyclin-E expression is high, in certain CHO cells there is a cell cycle having a relatively long $G_1$-phase and a short S-phase, and the cell growth is relatively high. The authors then cloned a cyclin-E expression vector into CHO cells. As a result of the then increased amount of cyclin-E, the transfected cell line exhibited higher proliferation rates than the non-transfected control cells, especially in protein-free basal media. In addition, the cell morphology and the cell cycle phase distribution were similar to the bFGF-stimulated CHO cells. Cell growth and morphology can therefore be influenced by this metabolic design of the cell cycle.

Bell et al. (1995) cloned a vector having a glutamine synthetase gene into a hybridoma cell line. Unlike the non-transfected control cell line, the transfected hybridoma cell line was able, as a result of its glutamine synthetase activity, to grow in a glutamine-free nutrient medium.

That transfection represented a crucial intervention in glutamine metabolism and therefore in the primary and energy metabolism of the mammalian cell. At the same time, the problem of toxicity caused by the ammonium formed from glutamine was significantly reduced by the possibility of glutamine-free culture.

Rees and Hay (1995) cloned the complete bacterial threonine metabolic pathway into a mammalian cell line, so that the cell line was able to grow in a threonine-free nutrient medium. The cell line was transfected with two vectors, which provided constitutive expression of the genes for aspartokinase, aspartate semialdehyde dehydrogenase, homoserine dehydrogenase, homoserine kinase and threonine synthetase. The complete bacterial biosynthesis pathway for threonine from aspartate was accordingly cloned into a mammalian cell line, the culture of which no longer requires the relatively expensive amino acid threonine. With high aspartate concentrations in a threonine-free medium, the transfected cell line exhibited the same growth behaviour as the non-transfected control cell line in a threonine-containing medium.

As a result of that metabolic engineering approach, it has been possible to produce nutrient media considerably more easily and more economically, without reducing growth and productivity at the same time.

A further metabolic engineering approach was aimed not at the direct primary metabolism but at glycosylation and thus the functionality and quality of glycoproteins such as, for example, EPO.

Schlenke et al. (1997) co-transfected a BHK cell line with vectors carrying the information for both 2,6-sialyltransferase and EPO. In comparison with a BHK cell line transfected with EPO-cDNA only, the EPO produced by that co-transfected cell culture exhibited a considerably increased N-acetylneuraminic acid content at the end of the carbohydrate side chains, which is attributable to the co-cloned 2,6-sialyltransferase.

In contrast to the 2,3-sialyltransferase occurring naturally in the BHK cell line, the 2,6-sialyltransferase can bind N-acetylneuraminic acid to N-acetylgalactosamine radicals of the carbohydrate side chains. With just that modification, the EPO has human-identical characteristics, which may be important for therapeutic use.

Analyses carried out by the inventors relating to the glucose substance flow in mammalian cell lines revealed a bottleneck in the initial reaction of glycolysis, which is catalysed by the enzyme hexokinase.

Using a metabolic engineering approach, the inventors have cloned a recombinant hexokinase gene from rat brain into BHK cells in order by means of additional hexokinase activity to extend the rate-determining reaction of glycolysis and to increase the substance flow and the amount of cell energy in the form of ATP.

In the recombinant cells, the hexokinase activity was up to three times higher than usual, glucose consumption rose, the substance flow in glycolysis increased and the intracellular ATP concentration also rose. Glutamine metabolism was also activated. However, the cell growth rate dropped in the case of the cell lines having high hexokinase activity and high ATP rates, whereas the cells' production rates for recombinant protein products rose. A high ATP content does not appear to promote the growth rates of the cells, but does possibly promote their productivity.

The results very clearly revealed a connection between glycolytic substance flow and cell growth: an increased relative or absolute glycolytic flow results in reduced cell growth or a reduced cell concentration, since it is probable that the flow of the pentose phosphate route is reduced and the formation of growth-reducing metabolites, such as UDP-N-acetylhexosamines, is increased.

However, a high ATP content also appears to be significant for the increase in productivity, since various steps of the protein biosynthesis may be directly associated with the concentration of ATP or GTP. For example, Jackson (1991) demonstrated that the translation rate for certain recombinant proteins is directly proportional to the availability of ATP.

Against this background, the relatively high product formation rate found by the inventors in cells having an increased ATP content was also explained.

All in all, therefore, the indication is that there is a direct association between the cellular ATP content or the amount of ATP produced and the production rate or amount of recombinant protein. The productivity of a cell could depend directly also on the ATP content and thus on the energy metabolism of the cell.

The problem underlying the invention is therefore to provide a method of improving the primary metabolism of mammalian cell lines.

According to the invention this problem is solved by a method of improving the primary energy metabolism of mammalian cell lines in accordance with patent claim 1.

The invention relates also to expression vectors for use in the method and also to recombinant mammalian cells, obtainable in accordance with the method, having primary energy metabolism that is improved in comparison with the wild type.

The recombinant cell lines obtained in accordance with the method of the invention exhibit increased full glucose oxidation, reduced lactate production, reduced glutamine consumption, a higher ATP content and higher oxygen consumption.

Furthermore, the recombinant cell lines grow in batch cultures for a considerably longer time than do wild-type cell lines and are sustained for longer by the available nutrient resources.

The recombinant cell lines are able to produce for a significantly longer period with the available nutrients, so that the total yield of the product rises and the process costs are reduced in comparison with conventional cell lines.

Further advantages that can be achieved using the method according to the invention will become clear in the course of the more detailed description which follows.

Advantageous and preferred embodiments of the invention are the subject of the subsidiary claims.

The invention will be described in more detail below with reference to the Figures.

In order to avoid the negative effect of a high glycolytic substance flow, while improving the utilisation of the glucose in terms of ATP production, it was necessary to adopt an approach different from that of the prior art.

Figure 1:
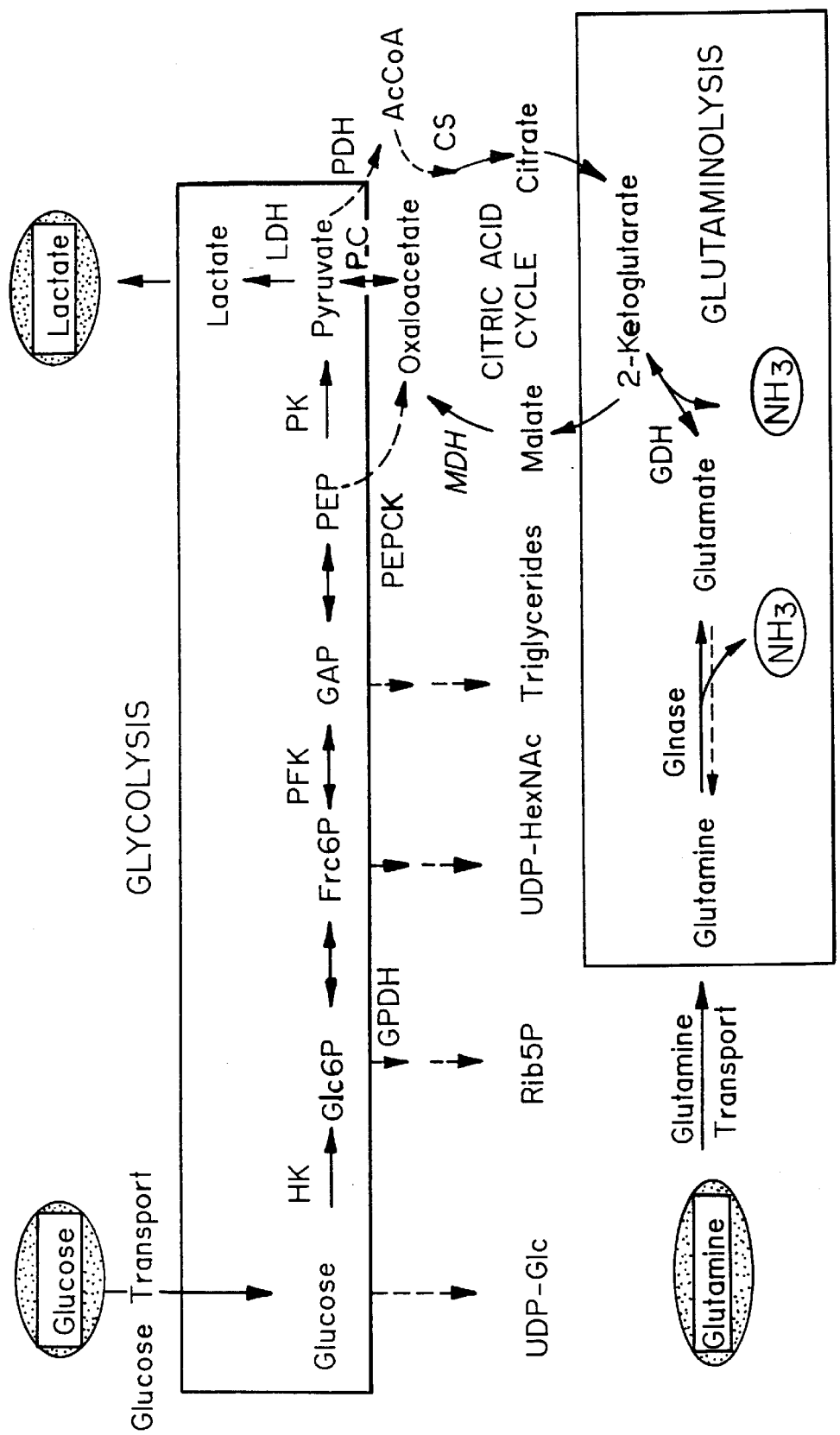
FIG. 1 is an overview of the primary metabolism in mammalian cells.
Figure 2A:
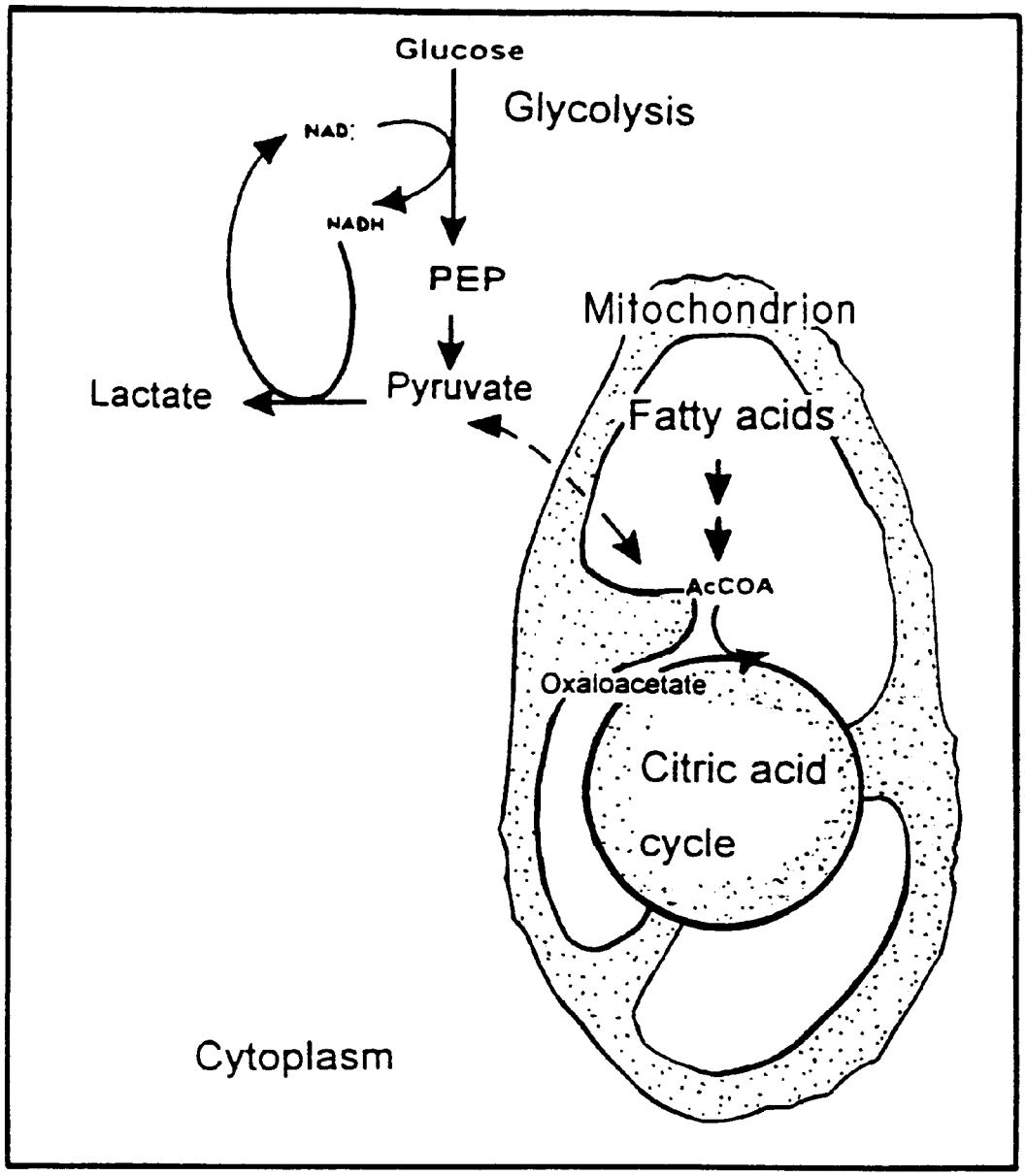
FIG. 2a is a diagram showing normal glucose oxidation in mammalian cell lines.

The premise for that approach was that the activities of all enzymes that connect glycolysis to the citric acid cycle, such as pyruvate dehydrogenase, phosphoenolpyruvate carboxylase and pyruvate carboxylase (PC), are present only to a small extent in cell lines, as compared with primary cells, or are not present at all (FIG. 2a).

In particular, the absence of pyruvate carboxylase is already well known as a hereditary disorder, the patients suffering from severe acidosis which results in an early death. In order to ensure the introduction of glucose carbon and pyruvate carbon into the citric acid cycle in the case of cell lines, according to the invention an additional metabolic secondary pathway was introduced by the insertion of a cytoplasmically expressed pyruvate carboxylase (PC).

The natural PC is expressed in the mitochondria and is strictly dependent upon the presence of sufficient amounts of acetyl-CoA. Since, however, the amount of acetyl-CoA in cell lines was considered critical because the supply of that metabolite by way of pyruvate is lacking, the approach via the increase in the gene dose, in analogy to the case of hexokinase, could not be taken in this instance.

In the yeast *Saccharomyces cerevisiae*, however, the pyruvate carboxylase is active even without the presence of acetyl-CoA (Colowick and Kaplan).

After the gene for PYC2 has been cleansed of yeast-specific sequences that could lead to expression problems in mammalian cells, an expression plasmid was transfected into BHK cells and expressed in the cytoplasm. The expression of a cytoplasmic pyruvate carboxylase (PYC2) from *Saccharomyces cerevisiae* represents the first instance of the successful expression of a yeast gene in mammalian cell lines.

Figure 2B:
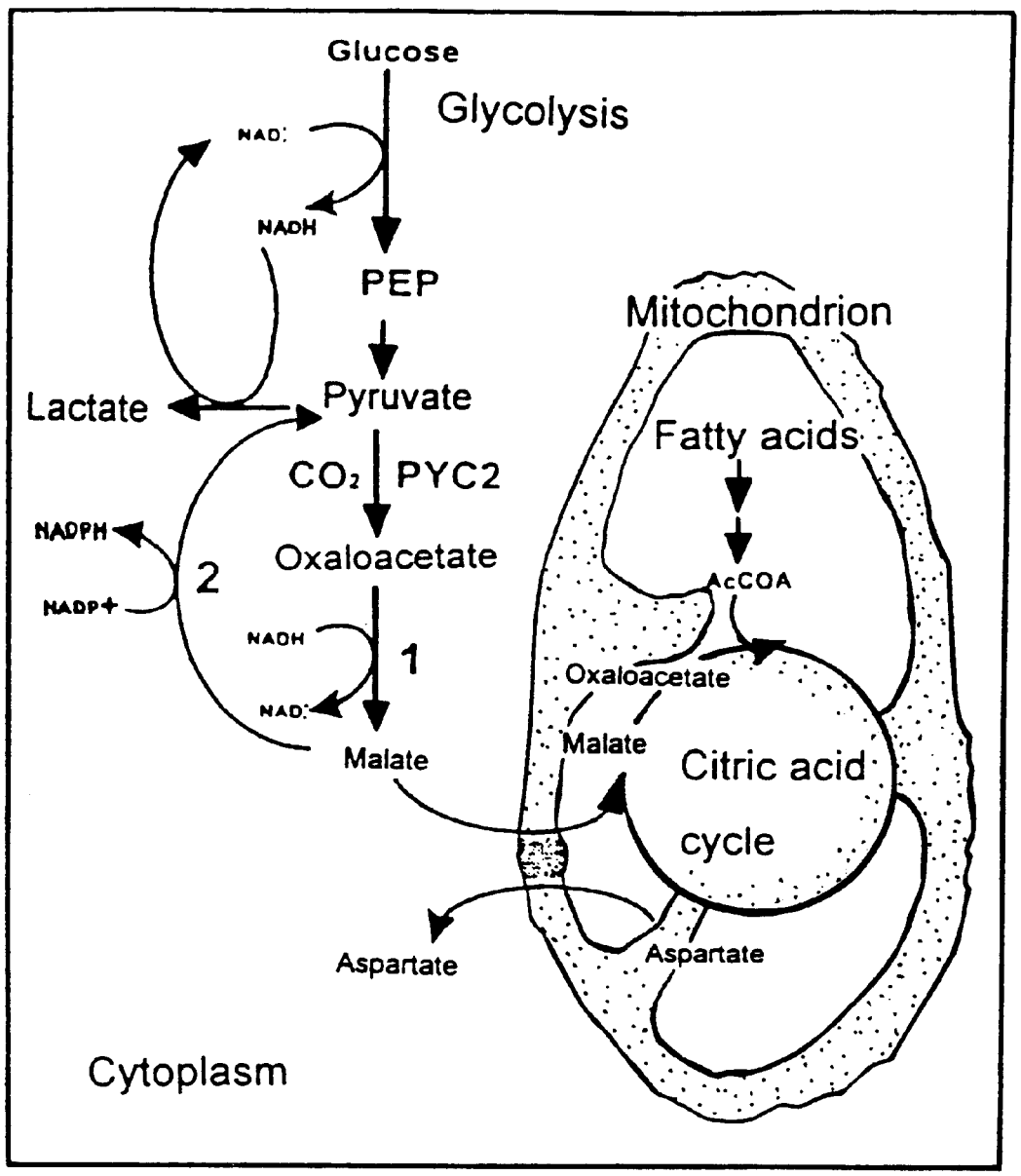
FIG. 2b shows the strategy according to the invention for a metabolic engineering procedure by the introduction into the cells of a cytosolically expressed pyruvate carboxylase gene (PYC2) from yeast according to a preferred embodiment of the invention.

This new step now makes it possible for the cells to convert the pyruvate from glycolysis while still in the cytoplasm first into oxaloacetate and then, by means of the cytoplasmic malate dehydrogenase already present, into malate, which can then be introduced via the malate-aspartate shuttle into the mitochondria for further oxidation (FIG. 2b).

FIG. 2a shows a diagrammatic representation of normal glucose oxidation in mammalian cell lines. In the mitochondria of primary cells, pyruvate is normally decarboxylated to acetyl-CoA by the pyruvate dehydrogenase complex (PDHC) and introduced into the citric acid cycle. In mammalian cell lines, little or no PDHC activity is found. The pyruvate carboxylase (PC) and phosphoenolpyruvate carboxykinase (PEPCK) activities are likewise very low.

FIG. 2b shows the strategy for a metabolic engineering procedure by the introduction into the cells of a cytosolically expressed pyruvate carboxylase gene (PYC2) from yeast. Pyruvate is then converted into oxaloacetate and introduced into the mitochrondria in the form of malate via the malate-aspartate shuttle. PYC2 competes with lactate dehydrogenase (LDH) for the cytoplasmic pyruvate pool, with the result that less substrate is available for lactate formation. Furthermore, $NAD^+$ is reconstituted by the cytoplasmic malate dehydrogenase ($MDH_{cyt}$). Furthermore, the back-reaction via the malic enzyme (ME) offers a further useful cycle for the formation of the important NADPH. $1=MDH_{cyt}$, $2=ME$.

With that step, three substantial advantages are achieved in the new recombinant cells:

1. More glucose carbon can be fully oxidised in the citric acid cycle.
2. The recombinant cytoplasmic pyruvate carboxylase competes with lactose dehydrogenase for the substrate pyruvate and takes away those amounts of substrate from the lactate formation.
3. The malate dehydrogenase reaction results in the back-formation of $NAD^+$ from NADH, which is available for glycolysis again at the stage of the glycerinaldehyde-3-phosphate dehydrogenase. That step reduces the significance of the lactate dehydrogenase reaction for the reconstitution of $NAD^+$. Depending upon the introduction rate of malate into the mitochondria via the shuttle mechanism it is possible, in addition, for an excess of malate to be decarboxylated, with the formation of NADPH, by the presence of the malic enzyme with reconstitution of pyruvate. NADPH is used for many synthesising processes and syntheses.

In the recombinant BHK cells, the consumption of glucose was reduced by a factor of 4, and the glutamine consumption was reduced twofold in comparison with the conventional BHK cells. Furthermore, a 1.4 times higher ATP content was demonstrated with comparably good growth (Tab. 1).

Confirmation that glucose carbon does in reality pass into the citric acid cycle was provided, with the aid of radioactively labelled glucose and pyruvate, by the release of radioactive $^{14}CO_2$ and substantiates higher oxidation of glucose.

The cell-specific oxygen consumption, which is an indication of the oxidative metabolism, rose by up to a factor of 3 in the case of the recombinant PYC2-expressing cell line in comparison with the original cell. The lower amounts of substrate consumed means that there is a higher amount of product per consumed substrate, so that it is now possible using these recombinant cell lines to produce pharmaproteins over a longer period with the available culture medium, which ultimately contributes to a reduction in the total manufacturing costs.

TABLE 1

Metabolism data for wild-type cells and PYC2-transfected cell clone cultures

| | Cell culture | | |
|---|---|---|---|
| Cell-specific metabolism data | Control cells | PYC2 cells | Improvement factor |
| glucose consumption/ (pmol s$^{-1}$ 10$^{-6}$) | 205 | 51 | 4.0 |
| glutamine consumption/ (pmol s$^{-1}$ 10$^{-6}$) | 48 | 27 | 1.8 |
| lactate production/ (pmol s$^{-1}$ 10$^{-6}$) | 332 | 130 | 2.6 |
| intracellular ATP content/fmol | 4.14 | 5.72 | 1.4 |
| O$_2$ consumption/ (pmol s$^{-1}$ 10$^{-6}$) | 35 | 102 | 2.9 |

For this purpose, in a manner known per se plasmids carrying the PYC2 gene from yeast were produced and BHK cells were accordingly transfected therewith. It will be apparent to the person skilled in the art that other cells can be used instead of the BHK cells. The success was verified by means of metabolism-specific data. The flux of glucose in the TCA is slightly raised. The oxygen consumption rate, an indication of the degree of oxidative phosphorylation, is likewise increased.

It has also been shown that the metabolically modified PYC-carrying recombinant cells have a lower consumption of glucose and glutamine. At the same time, the lactate production rate drops. As a consequence, the growth cycle of the PYC cells in batch culture is lengthened in comparison with the unmodified cells. For batch fermentation this results in improved utilisation of substrate and thus a prolonged production phase.

In continuous cultures, the inventors were able to show that as a result of the reduced consumption of substrate by the recombinant cells, the improved utilisation of the substrate leads to a higher cell concentration in the steady-state equilibrium of the chemostat.

In future, using EPO as model protein, it is to be investigated whether the cell-specific productivity or the space-time yield in the fermenter can be increased.

Preparation of the Gene Construct

The cDNA of pyruvate carboxylase (PYC2, isoenzyme 2) from Saccharomyces cerevisiae was obtained from R. Stucka (Stucka et al., 1991). In order to avoid possible interactions of the yeast vector fragment bordering the coding region, the cDNA was trimmed down to the essential coding sequences by endonuclease restriction and ligation with small PCR fragments according to a procedure well known in the art (FIG. 3).

The modified cDNA was placed under the transcription control of a CMV promoter. The resulting pCMVPYC2 plasmid also contains an ampicillin-resistance gene. It will be clear that other promoters and resistance genes or generally selection markers can be used.

Figure 3:
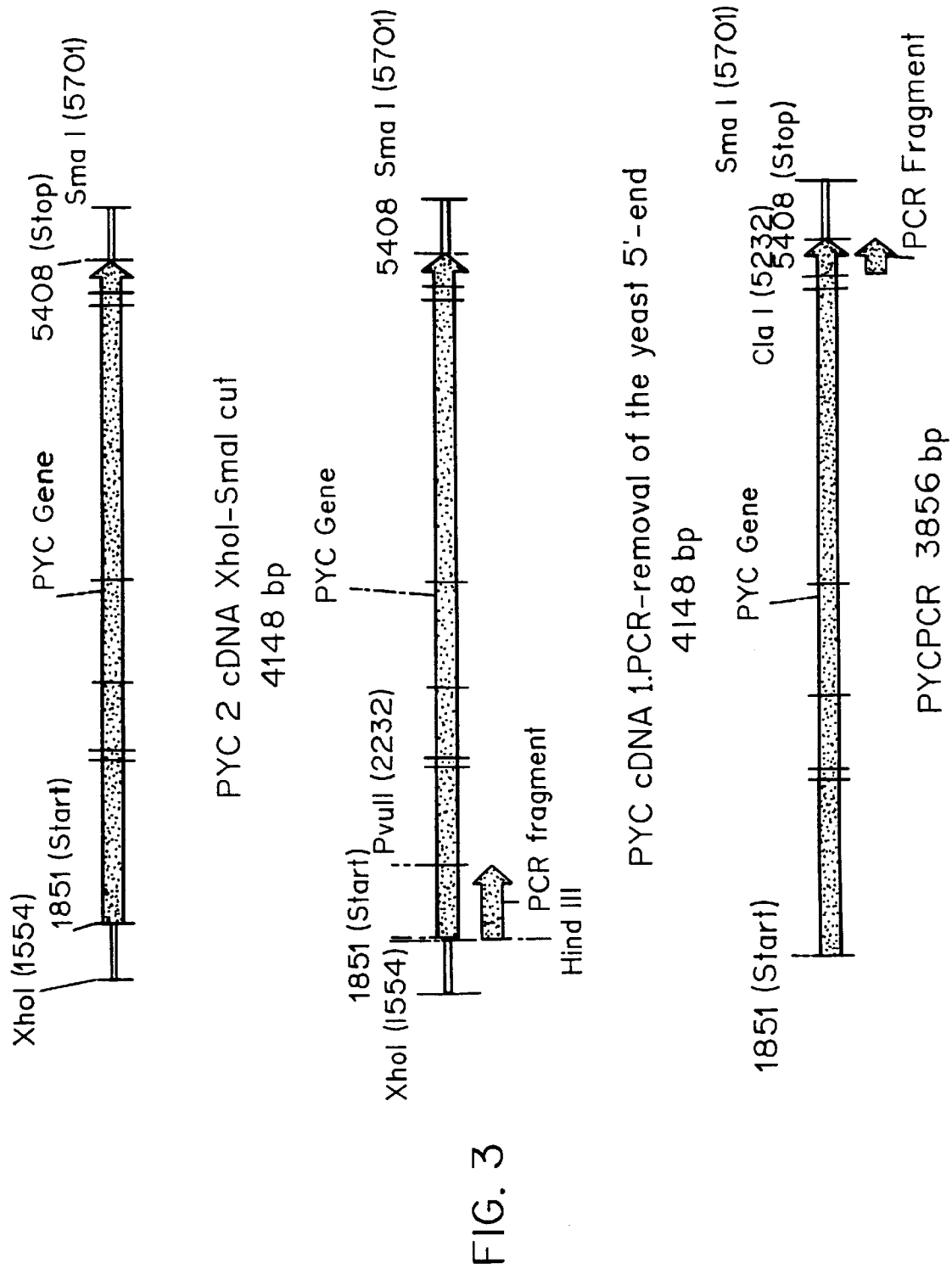
FIG. 3 shows the removal of flanking yeast-specific sequences from the 5'- and 3'-regions of the PYC2 gene.

FIG. 3 shows the removal of flanking yeast-specific sequences from the 5'- and 3'-regions of the PYC2 gene.

First using PvuII a 678 bp fragment was cut out from the 5'-end, the missing 381 bp were ligated by means of PCR (polymerase chain reaction) via specific primers and a HindIII restriction site was built on before the coding sequence.

For the 3'-end, a corresponding procedure was carried out via the ClaI restriction site by removal of 469 bp and ligation with a fragment 176 bp long. The fragment was provided with a HindIII and SmaI restriction site at the 3'-end.

Preparation of the Recombinant BHK Cells

Figure 4:
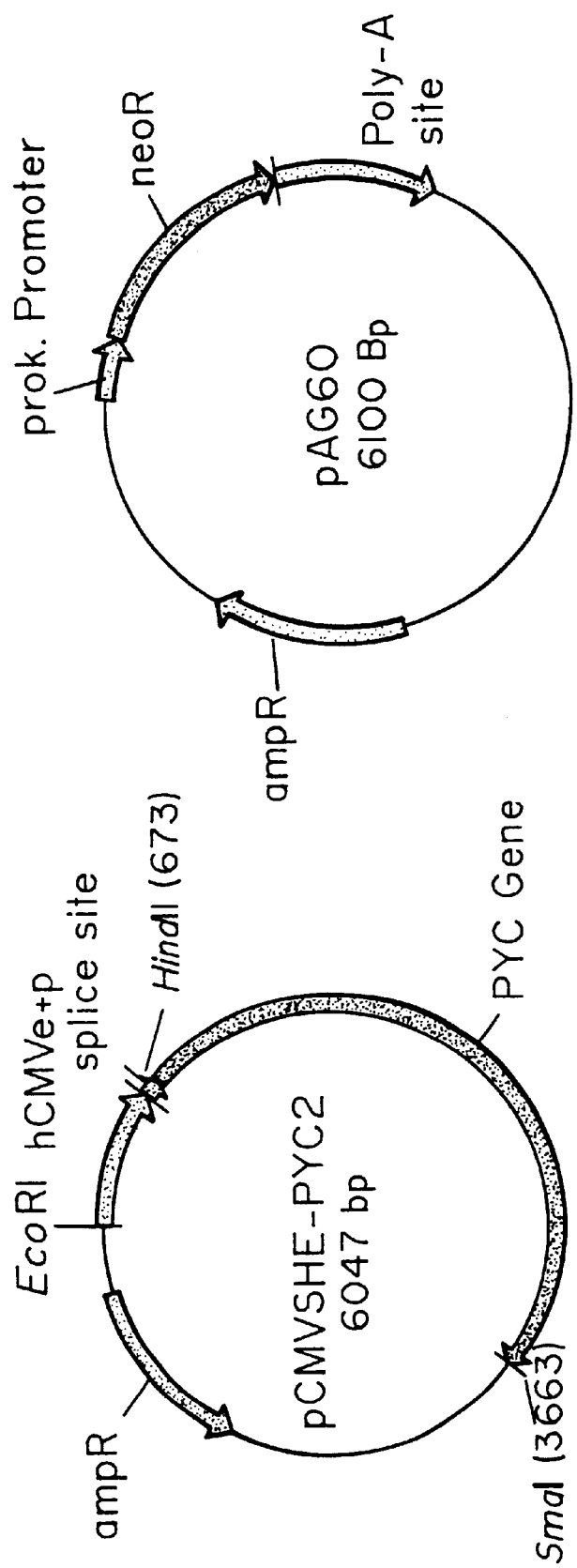
FIG. 4 is a diagrammatic drawing of the expression vector pCMVSHE-PYC2 and of the selection vector pAG60.

The plasmid pCMVSHE-PYC2 was transfected with a neomycin resistance plasmid (pAG60) with the aid of the calcium phosphate coprecipitation method (Maitland and McDougall, 1977) into BHK-21A cells in accordance with a modified protocol of Kriegler (Kriegler, 1990) (FIG. 4). After removal of the precipitates, osmotic shock by the addition of glycine was not applied. The latter measures may be carried out, however, when the practical circumstances require it. It is also possible to use other transfection procedures known in the art.

FIG. 4 is a diagrammatic drawing of the expression vector pCMVSHE-PYC2, based on the standard expression vector pCMVSHE. The meanings are as follows: CMV: Cytomegalovirus immediate early enhancer promoter; SVpA: late polydenylation signal, splice sites, SV40 early late splice sites.

Bibliography

Bell, S. L., Bebbington, C., Scott, M. F., Wardell, J. N., Spier, R. E., Bushell, M. E., Sanders, P. G. 1995. Genetic Engineering of Hybridoma Glutamine Metabolism. Enzyme Microb. Technol. 17: 98–106

Fitzpatrick, L., Jenkins, H. A., Butler, M. 1993. Glucose and glutamine metabolism of a murine B-lymphocyte hybridoma grown in batch culture. Appl. Biochem. Biotech. 43: 93–116

Gawlitzek, M., Valley, U., Wagner, R. 1998. Ammonium ion/glucosamine dependent increase of oligosaccharide complexity in recombinant glycoproteins secreted from cultivated BHK-21 cells. Biotechnol. Bioeng. 57: 518–528

Grammatikos, S. I., Valley, U., Nimtz, M., Conrad, H. S., Wagner, R. 1998. Intracellular UDP-N-acetyl-hexosamine pool affects N-glycane complexity: A mechanism of ammonium action on protein glycosylation. Biotechnol. Progr. 14: 410–419

Jackson, R. J. 1991. The ATP requirement for initiation of eukaryotic translation varies according to the mRNA species. Eur. J. Biochem. 200: 285–294

Kriegler, M. 1990. Gene transfer and expression—a laboratory manual. Stockton Press London Maitland, N. J., McDougall, J. K. 1977. Biochemical transformation of mouse cells by fragments of herpes simplex virus DNA. Cell 11: 233–241

Neermann, J., Wagner, R. 1996. Comparative Analysis of Glucose and Glutamine Metabolism in Transformed Mammalian Cell Lines, Insect and Primary Liver Cells. J. Cell. Physiol. 166: 152–169

Pendse, G. J., Bailey, J. E. 1994. Effect of Vitreoscilla hemoglobin expression on growth and specific tissue plasminogen activator productivity in recombinant Chinese hamster ovary cells. Biotechnol. Bioeng. 44: 1367–1370

Petch, D., Butler, M. A. 1994. Profile of energy metabolism in a murine hybridoma: Glucose and glutamine utilization. J. Cell. Physiol. 161: 71–76

Rees, W. D., Hay, S. M. 1995 The biosynthesis of threonine by mammalian cells: expression of a complete bacterial biosynthetic pathway in an animal cell. Biochem. J. 309: 999–1007

Renner, W. A., Lee, K. H., Hatzimanikatis, V., Bailey, J. E., Eppenberger, H. M. 1995. Recombinant Cyclin E Expression Activates Proliferation and Obviates Surface Attachment of Chinese Hamster Ovary (CHO) Cells in Protein-Free Medium. Biotechnol. Bioeng. 47: 476–482

Ryll, T., Valley, U., Wagner, R. 1994. Biochemistry of Growth Inhibition by Ammonium Ions in Mammalian Cells. Biotechnol. Bioeng. 44: 184–193

Schlenke, P., Grabenhorst, E., Wagner, R., Nimtz, M., Conradt, H. S. 1997. Expression of human 2,6-sialyl-transferase in BHK-21A cells increases the sialylation of coexpressed human erythropoietin. In: Animal Cell Technology: From Vaccines to Genetic Medicine (Carrondo, M. J. T., Griffiths, J. B., Moreira, J. L. P, Eds.), Kluwer Academic Publishers, Dordrecht, pp. 475–480

Stucka, R., Dequin, S., Salmon, J. M., Gancedo, C. 1991. DNA sequences in chromosomes II and VII code for pyruvate carboxylase isoenzymes in Saccharomyces cerevisiae; analysis of pyruvate carboxylase-deficient strains. Mol. Gen. Genet. 229: 307–315

Valley, U., Nimtz, M., Conradt, H. S., Wagner. R. 1999. Incorporation of Ammonium into Intracellular UDP-Activated N-acetylhexosamines and into Carbohydrate Structures in Glycoproteins. Biotechnol. Bioeng., in press Colowick, S. P., Kaplan, N. O., 1969. Pyruvate carboxylase from Saccharomyces cerevisiae. In: Citric acid cycle of: Methods in Enzymology (Lowenstein, J. M., ed.), Vol. XIII.

What is claimed is:

1. A recombinant mammalian cell having an improved energy metabolism produced according to a method comprising:

i) transforming or transfecting said cell with an expression vector of comprising a structural gene for a yeast cytoplasmic pyruvate carboxylase, a suitable promoter for transcription control in said mammalian cell and one or more selectable markers;

ii) culturing the transformed cells under conditions suitable for expression and selection; and iii) selecting and isolating surviving cell clones.

2. The recombinant mammalian cell of claim 1, wherein said yeast cytoplasmic pyruvate carboxylase is derived from *Saccharomyces cerevisiae*.

3. The recombinant mammalian cell of claim 1, wherein said promoter is the CMV promoter.

4. The recombinant mammalian cell of claim 1, wherein said selection marker is an ampicillin resistance gene.

5. The recombinant mammalian cell of claim 1, wherein said selection marker is a geneticin resistance gene.

6. The recombinant mammalian cell of claim 1, wherein said cell is a BHK cell.

7. The recombinant mammalian cell of claim 1, wherein said method further comprises culturing said surviving cell clones.

8. The recombinant mammalian cell of claim 1, wherein said method further comprises using said surviving cell clones in formentation.

9. The recombinant mammalian cell of claim 1, wherein said cell exhibits increased full glucose oxidation as compared to a wild-type mammalian cell of the same origin.

10. The recombinant mammalian cell of claim 1, wherein said cell exhibits reduced lactate production as compared to a wild-type mammalian cell of the same origin.

11. The recombinant mammalian cell of claim 1, wherein said cell exhibits reduced glutamine consumption as compared to a wild-type mammalian cell of the same origin.

12. The recombinant mammalian cell of claim 1, wherein said cell exhibits an increased ATP content as compared to a wild-type mammalian cell of the same origin.

13. The recombinant mammalian cell of claim 1, wherein said cell exhibits an increased oxygen consumption as compared to a wild-type mammalian cell of the same origin.

14. The recombinant mammalian cell of claim 1, wherein said growth of said cell is sustained for a longer period of time on a finite culture condition as compared to a wild-type mammalian cell of the same origin under the same culture conditions.

15. The recombinant mammalian cell of claim 1, wherein said cell provides an increased yield of product compared to a cell that has not been transformed with an expression construct comprising a structural gene for a yeast cytoplasmic pyruvate carboxylase.

\* \* \* \* \*